(12) United States Patent
Gatzemeyer et al.

(10) Patent No.: US 7,845,041 B2
(45) Date of Patent: *Dec. 7, 2010

(54) INTERACTIVE MUSICAL TOOTHBRUSH

(75) Inventors: John J. Gatzemeyer, Hillsborough, NJ (US); Eduardo J. Jimenez, Manalapan, NJ (US); Robert Riebe, Minneapolis, MN (US); James E. Michaels, Downers Grove, IL (US); Eugene Eighmy, Birmingham, AL (US); Evan Ward, Chicago, IL (US)

(73) Assignee: Colgate-Palmolive Company, New York, NY (US)

( * ) Notice: Subject to any disclaimer, the term of this patent is extended or adjusted under 35 U.S.C. 154(b) by 696 days.

This patent is subject to a terminal disclaimer.

(21) Appl. No.: 11/677,433

(22) Filed: Feb. 21, 2007

(65) Prior Publication Data
US 2007/0192976 A1 Aug. 23, 2007

Related U.S. Application Data

(63) Continuation-in-part of application No. 11/413,624, filed on Apr. 28, 2006, now Pat. No. 7,418,757.

(60) Provisional application No. 60/738,528, filed on Nov. 21, 2005, provisional application No. 60/677,192, filed on May 3, 2005.

(51) Int. Cl.
*A46B 15/00* (2006.01)
(52) U.S. Cl. ......................................... 15/105; 15/167.1
(58) Field of Classification Search ................... 15/105, 15/167.1, 22.1
See application file for complete search history.

(56) References Cited

U.S. PATENT DOCUMENTS

| | | | |
|---|---|---|---|
| 1,986,955 A | 1/1935 | Bedell |
| 2,877,477 A | 3/1959 | Levin |
| 2,947,013 A | 8/1960 | Silverman |
| 3,027,507 A | 3/1962 | Hubner |
| 3,458,794 A | 7/1969 | Bohnstedt |
| 4,075,458 A | 2/1978 | Moyer |
| 4,341,230 A | 7/1982 | Siahou |
| 4,479,516 A | 10/1984 | Hunter |
| 4,603,448 A | 8/1986 | Middleton et al. |
| 4,698,869 A | 10/1987 | Mierau et al. |
| 4,716,614 A | 1/1988 | Jones et al. |
| 4,744,124 A | 5/1988 | Wang |

(Continued)

FOREIGN PATENT DOCUMENTS

CA 2267732 10/2000

(Continued)

OTHER PUBLICATIONS

International Search Report Dated (Sep. 29, 2008).

(Continued)

*Primary Examiner*—Shay L Karls
(74) *Attorney, Agent, or Firm*—Amy M. Fernandez (57) ABSTRACT

A toothbrush includes a storage unit having an input, a memory for storing audio signals received via the input. The unit can have an output for transmitting or playing the stored audio signals. A variety of different constructions of storage unit and toothbrush configurations are described, each creating an environment that makes tooth brushing enjoyable.

22 Claims, 7 Drawing Sheets

U.S. PATENT DOCUMENTS

| | | |
|---|---|---|
| 4,764,961 A | 8/1988 | Hung |
| 4,766,630 A | 8/1988 | Hegemann |
| 4,788,734 A | 12/1988 | Bauer |
| 4,845,796 A | 7/1989 | Mosley |
| 4,866,807 A | 9/1989 | Kreit |
| 4,944,016 A | 7/1990 | Christian |
| 4,944,704 A | 7/1990 | Grace |
| 5,006,779 A | 4/1991 | Fenne |
| 5,044,037 A | 9/1991 | Brown |
| D321,986 S | 12/1991 | Snyder et al. |
| 5,115,533 A | 5/1992 | Hukuba |
| 5,133,102 A | 7/1992 | Sakuma |
| 5,165,131 A | 11/1992 | Staar |
| D340,455 S | 10/1993 | Christian |
| 5,259,086 A | 11/1993 | Fong |
| 5,314,336 A | 5/1994 | Diamond et al. |
| 5,335,798 A | 8/1994 | Bonwell |
| 5,337,435 A | 8/1994 | Krasner |
| 5,339,479 A | 8/1994 | Lyman |
| 5,341,534 A | 8/1994 | Serbinski et al. |
| D353,490 S | 12/1994 | Hartwein |
| D354,168 S | 1/1995 | Hartwein |
| 5,438,726 A | 8/1995 | Leite |
| D363,605 S | 10/1995 | Kou et al. |
| 5,493,747 A | 2/1996 | Inakagata et al. |
| 5,504,961 A | 4/1996 | Yang |
| D371,242 S | 7/1996 | Shimatsu et al. |
| D373,023 S | 8/1996 | Otero et al. |
| 5,544,382 A | 8/1996 | Giuliani |
| D375,841 S | 11/1996 | Serbinski |
| 5,572,762 A | 11/1996 | Scheiner |
| 5,628,641 A | 5/1997 | Hahn |
| 5,673,451 A | 10/1997 | Moore et al. |
| 5,675,859 A | 10/1997 | Barre |
| 5,697,117 A | 12/1997 | Craft |
| D388,958 S | 1/1998 | Hartwein |
| 5,704,087 A | 1/1998 | Strub |
| 5,784,742 A | 7/1998 | Giuliani et al. |
| 5,786,749 A | 7/1998 | Johnson |
| D397,252 S | 8/1998 | Allende |
| 5,810,601 A | 9/1998 | Williams |
| D403,511 S | 1/1999 | Serbinski |
| 5,864,288 A * | 1/1999 | Hogan .................... 340/568.1 |
| 5,894,453 A | 4/1999 | Pond |
| 5,901,397 A | 5/1999 | Hafele et al. |
| 5,924,159 A | 7/1999 | Haitin |
| 5,960,507 A | 10/1999 | Dutra |
| 5,974,616 A | 11/1999 | Dreyfus |
| 5,994,855 A | 11/1999 | Lundell et al. |
| 6,029,303 A | 2/2000 | Dewan |
| D426,708 S | 6/2000 | Francis |
| 6,081,957 A | 7/2000 | Webb |
| 6,115,477 A | 9/2000 | Filo |
| 6,154,912 A | 12/2000 | Li |
| D436,254 S | 1/2001 | Kling et al. |
| 6,199,239 B1 | 3/2001 | Dickerson |
| 6,202,242 B1 | 3/2001 | Salmon et al. |
| 6,202,245 B1 | 3/2001 | Khodadadi |
| D440,766 S | 4/2001 | Hartwein et al. |
| 6,237,178 B1 | 5/2001 | Krammer et al. |
| 6,325,066 B1 | 12/2001 | Hughes |
| D453,996 S | 3/2002 | Kling et al. |
| D455,556 S | 4/2002 | Kling |
| 6,389,633 B1 | 5/2002 | Rosen |
| D458,028 S | 6/2002 | McCurrach |
| 6,397,424 B1 | 6/2002 | Leung |
| 6,421,866 B1 | 7/2002 | McDougall |
| D467,432 S | 12/2002 | Callendrille, Jr. |
| 6,536,068 B1 | 3/2003 | Yang |
| 6,554,619 B2 | 4/2003 | Williams |
| D474,895 S | 5/2003 | Breit |
| D475,529 S | 6/2003 | Wright et al. |
| 6,581,233 B1 | 6/2003 | Cheng |
| D476,485 S | 7/2003 | Mulder et al. |
| D478,423 S | 8/2003 | Mulder et al. |
| 6,606,755 B1 | 8/2003 | Robinson et al. |
| 6,611,780 B2 | 8/2003 | Lundell |
| 6,619,969 B2 | 9/2003 | Scheider |
| D480,563 S | 10/2003 | Hensel |
| 6,633,747 B1 | 10/2003 | Reiss |
| 6,648,641 B1 | 11/2003 | Viltro |
| D484,312 S | 12/2003 | Li |
| 6,658,687 B1 | 12/2003 | McDonald |
| D489,183 S | 5/2004 | Akahori et al. |
| D489,534 S | 5/2004 | Hensel |
| 6,731,213 B1 | 5/2004 | Smith |
| D492,118 S | 6/2004 | McCurrach et al. |
| D493,960 S | 8/2004 | Jimenez et al. |
| 6,779,216 B2 | 8/2004 | Davies et al. |
| D496,653 S | 9/2004 | Townsend et al. |
| 6,792,640 B2 | 9/2004 | Lev |
| 6,795,993 B2 | 9/2004 | Lin |
| 6,799,346 B2 | 10/2004 | Jeng et al. |
| 6,826,350 B1 * | 11/2004 | Kashino et al. ............... 386/46 |
| D500,207 S | 12/2004 | Jimenez et al. |
| D500,208 S | 12/2004 | Vu |
| D500,209 S | 12/2004 | Kellogg |
| 6,836,918 B1 | 1/2005 | Wong |
| 6,845,537 B2 | 1/2005 | Wong |
| D502,601 S | 3/2005 | Lamason et al. |
| D503,537 S | 4/2005 | Lamason et al. |
| D503,852 S | 4/2005 | Hensel |
| 6,883,199 B1 | 4/2005 | Lundell et al. |
| 6,920,660 B2 | 7/2005 | Lam |
| 6,923,409 B2 | 8/2005 | Strunk |
| D510,930 S | 10/2005 | Deguchi |
| 6,952,855 B2 | 10/2005 | Lev et al. |
| 6,954,961 B2 | 10/2005 | Ferber et al. |
| D511,519 S | 11/2005 | Bone et al. |
| D515,815 S | 2/2006 | Jimenez et al. |
| D515,816 S | 2/2006 | Jimenez et al. |
| 7,003,839 B2 * | 2/2006 | Hafliger et al. ............... 15/22.1 |
| 7,013,522 B2 | 3/2006 | Kumagai |
| 7,055,531 B2 | 6/2006 | Rehkemper |
| 7,086,111 B2 | 8/2006 | Hilscher et al. |
| D529,044 S | 9/2006 | Andre et al. |
| D531,190 S | 10/2006 | Lee et al. |
| 7,120,960 B2 | 10/2006 | Hilscher et al. |
| D533,349 S | 12/2006 | Jimenez et al. |
| D533,720 S | 12/2006 | Vu |
| D534,726 S | 1/2007 | Vu |
| D534,728 S | 1/2007 | Vu |
| D534,921 S | 1/2007 | Andre et al. |
| D535,308 S | 1/2007 | Andre et al. |
| D538,267 S | 3/2007 | Christianson et al. |
| D538,297 S | 3/2007 | Ching |
| D539,813 S | 4/2007 | Chen |
| 7,418,757 B2 | 9/2008 | Gatzerneyer et al. |
| 2001/0004428 A1 | 6/2001 | Horng |
| 2002/0067084 A1 | 6/2002 | Jung |
| 2002/0174498 A1 | 11/2002 | Li |
| 2003/0017874 A1 | 1/2003 | Jianfei |
| 2003/0221269 A1 | 12/2003 | Zhuan |
| 2003/0232303 A1 | 12/2003 | Black |
| 2004/0000017 A1 | 1/2004 | Kumagai |
| 2004/0074026 A1 | 4/2004 | Blaustein et al. |
| 2004/0123409 A1 | 7/2004 | Dickie |
| 2004/0134000 A1 | 7/2004 | Hilfinger et al. |
| 2004/0163191 A1 | 8/2004 | Cuffaro et al. |
| 2004/0255409 A1 | 12/2004 | Hilscher |
| 2005/0000537 A1 | 1/2005 | Junkins |
| 2005/0011022 A1 | 1/2005 | Kwong |
| 2005/0022322 A1 | 2/2005 | Jimenez et al. |
| 2005/0066461 A1 | 3/2005 | Chang |

| | | | |
|---|---|---|---|
| 2005/0144744 A1 | 7/2005 | Thiess et al. | |
| 2005/0150067 A1 | 7/2005 | Cobabe et al. | |
| 2005/0152231 A1 | 7/2005 | Yeh | |
| 2005/0172433 A1 | 8/2005 | Oliver | |
| 2005/0204490 A1 | 9/2005 | Kemp et al. | |
| 2005/0278882 A1* | 12/2005 | Drzewiecki et al. | 15/105 |
| 2005/0283929 A1 | 12/2005 | Jimenez et al. | |
| 2006/0037158 A1 | 2/2006 | Foley et al. | |
| 2006/0048315 A1 | 3/2006 | Chan et al. | |
| 2006/0104456 A1 | 5/2006 | Filo et al. | |
| 2006/0123570 A1 | 6/2006 | Pace et al. | |
| 2006/0130253 A1 | 6/2006 | Rycroft | |
| 2006/0150350 A1 | 7/2006 | Pfenniger et al. | |
| 2006/0179591 A1 | 8/2006 | Spooner | |
| 2007/0039109 A1 | 2/2007 | Nanda | |
| 2007/0074359 A1 | 4/2007 | O'Lynn | |
| 2007/0094822 A1 | 5/2007 | Gatzerneyer | |
| 2007/0190509 A1 | 8/2007 | Kim | |
| 2007/0192976 A1 | 8/2007 | Gatzemeyer | |
| 2007/0261185 A1 | 11/2007 | Guney et al. | |
| 2008/0028553 A1 | 2/2008 | Batthauer | |

FOREIGN PATENT DOCUMENTS

| | | |
|---|---|---|
| CA | 2409908 | 11/2002 |
| CA | 2499371 | 4/2004 |
| CA | 2530337 | 1/2005 |
| CA | 2545676 | 5/2005 |
| CA | 2553568 | 9/2005 |
| CA | 2508994 | 12/2005 |
| CA | 2559039 | 6/2006 |
| CA | 2589817 | 6/2006 |
| CA | 2591798 | 7/2006 |
| CN | 2461373 | 11/2001 |
| CN | 2537277 | 2/2003 |
| CN | ZL03257211.5 | 5/2003 |
| CN | 1470205 | 1/2004 |
| CN | 2614048 | 5/2004 |
| CN | ZL03364715.1 | 5/2004 |
| CN | 1556994 | 12/2004 |
| CN | ZL200620092422 | 7/2006 |
| CN | ZL200630116898.5 | 7/2007 |
| DE | 3149233 | 4/1983 |
| DE | 19811676 | 9/1999 |
| DE | 29915858 U1 | 1/2000 |
| EP | 0 435 329 | 7/1991 |
| EP | 0634151 | 1/1995 |
| EP | 1609389 | 12/2005 |
| EP | 1609389 A | 12/2005 |
| EP | 1698252 A | 9/2006 |
| JP | 01008914 | 1/1989 |
| JP | 2003180717 | 7/2003 |
| JP | 2004065838 | 3/2004 |
| JP | 2004105246 | 4/2004 |
| WO | WO 98/55274 | 12/1998 |
| WO | WO 99/32011 | 7/1999 |
| WO | WO 00/74591 | 12/2000 |
| WO | WO03085670 | 10/2003 |
| WO | WO 2004/026077 | 4/2004 |
| WO | WO 2004/098445 | 11/2004 |
| WO | WO2005074745 | 8/2005 |
| WO | WO 2006/002101 | 1/2006 |
| WO | 2006057513 A | 6/2006 |
| WO | WO9700650 | 6/2006 |
| WO | WO2006065159 | 6/2006 |
| WO | 2006119205 A | 11/2006 |
| WO | WO2006137648 | 12/2006 |
| WO | WO2007032015 | 3/2007 |
| WO | WO2007068984 | 6/2007 |
| WO | WO2007089638 | 8/2007 |
| WO | WO2007097886 | 8/2007 |
| WO | WO2007106757 | 9/2007 |

OTHER PUBLICATIONS

"iBrush—the toothbrush that makes you never want to stop brushing your teeth". http://www.cs.chalmers.se.idc/ituniv/student/2003/ubicomp/ibrush.htm. Published 2003. Retrieved May 19, 2006.

* cited by examiner

INTERACTIVE MUSICAL TOOTHBRUSH

CROSS-REFERENCE TO RELATED APPLICATIONS

This application is a continuation-in-part of U.S. patent application Ser. No. 11/413,624 filed, Apr. 28, 2006, now U.S. Pat. No. 7,418,757 which claims the benefit of priority of U.S. Provisional Application 60/738,528, filed Nov. 21, 2005, and U.S. Provisional Application 60/677,192, filed May 3, 2005, all of which are incorporated by reference herein in their entirety.

FIELD OF THE INVENTION

The present invention relates to toothbrushes, and more particularly to a toothbrush that can record and/or play music or other audio signals.

BACKGROUND OF THE INVENTION

Statistics show that only a small percentage of the population in any country brushes their teeth for the dentist recommended time of two minutes. This can be especially true of younger children and teenagers, who view tooth brushing as a mundane duty with few pleasurable aspects. Accordingly, there is a need to create an environment that makes tooth brushing enjoyable so that children and teenagers in particular will brush as often as they should and for the recommended period of time.

BRIEF SUMMARY OF THE INVENTION

The present invention enables a person to know that he/she has brushed his/hers teeth for a period of time close to the professional recommendation while enjoying a musical interlude of his/her choosing.

In one aspect, a toothbrush is provided with the ability to record, store, and play music by way of logic control circuitry and a speaker.

In another aspect, a toothbrush comprises a processor configured to automatically record an audio signal from an external audio source upon detection of sound outputted from the external audio source.

In one aspect, a toothbrush may comprise an oral care region with a body, a storage unit having an input connection, a digital memory for storing audio signals received via the input connection, and an output for transmitting or playing the stored audio signals.

In one aspect, a toothbrush includes a latching door to permit insertion of the detachable storage unit therein.

In another aspect, a storage unit includes a microprocessor configured to automatically record the one or more signals from an external signal source. In one arrangement, the automatic recording occurs upon detection of sound outputted from an external signal source.

In yet another aspect, a method provides for outputting audio signals from an oral care device. The method includes but is not limited to determining that an input of a storage unit has been connected to an output of a source device; detecting an audible signal from the source device; and automatically recording the audible signal in a memory of the storage unit.

A variety of different storage unit and toothbrush configurations are discussed herein, each creating an enjoyable environment during tooth brushing. These configurations advantageously provide improved oral hygiene for children and teenagers.

DETAILED DESCRIPTION OF THE INVENTION

The following detailed description is not intended to be understood in a limiting sense, but to be an example of the invention presented solely for illustration thereof, and by reference to which in connection with the following description and the accompanying drawings one skilled in the art may be advised of the advantages and construction of the invention. In the various views of the drawings, like reference characters designate like or similar parts.

FIGS. 1-4 illustrate a toothbrush assembly 100 in accordance with at least one aspect of the present invention. The toothbrush assembly 100 includes a power toothbrush 120 having a body 125, a removable storage unit 140 that forms a portion of the handle 126, a first power button 128 and a second power button 129. The toothbrush 120 further comprises a head 124 or oral care region having tooth cleaning elements 127, and a handle 126. Head 124 may be replaceable, or it may be permanently attached to handle 126. As used herein, the term "tooth cleaning elements" or "cleaning elements" includes any type of structure that is commonly used or is suitable for use in providing oral health benefits (e.g., tooth cleaning, tooth polishing, tooth whitening, massaging, stimulating, etc.) by making contact with portions of the teeth and gums. Such tooth cleaning elements include but are not limited to tufts of bristles that can be formed to have a number of different shapes and sizes and elastomeric cleaning members that can be formed to have a number of different shapes and sizes, or a combination of both tufts of bristles and elastomeric cleaning members. The tooth cleaning elements may be arranged on head 124 as desired.

Figure 1:
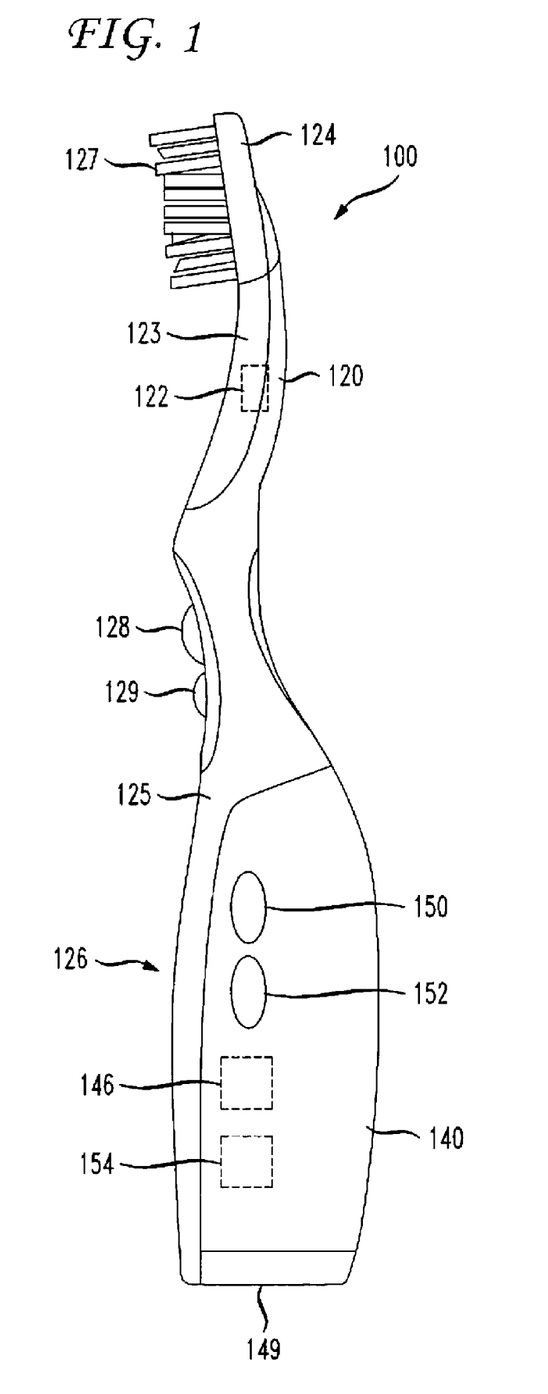
FIG. 1 is a side view of an example of a toothbrush in accordance with at least one aspect of the present invention.

The toothbrush 120 may be a powered toothbrush including a power source that drives a powered element, such as movable cleaning elements 127 with a single activation/deactivation or "on/off" button 128. In an alternative configuration, toothbrush 120 may be a power toothbrush including a power source that drives a powered element, such as movable cleaning elements 127 with an activation or "on" button 128 and a deactivation or "off" button 129.

Figure 2:
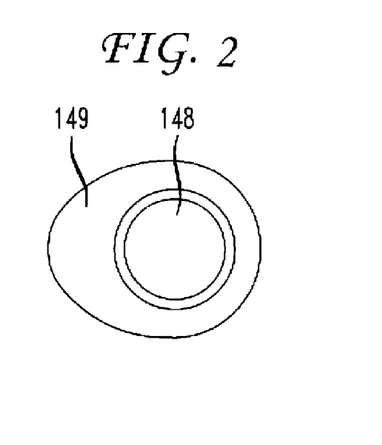
FIG. 2 is a bottom view of the surface of the toothbrush of FIG. 1 in accordance with at least one aspect of the present invention.
Figure 3:
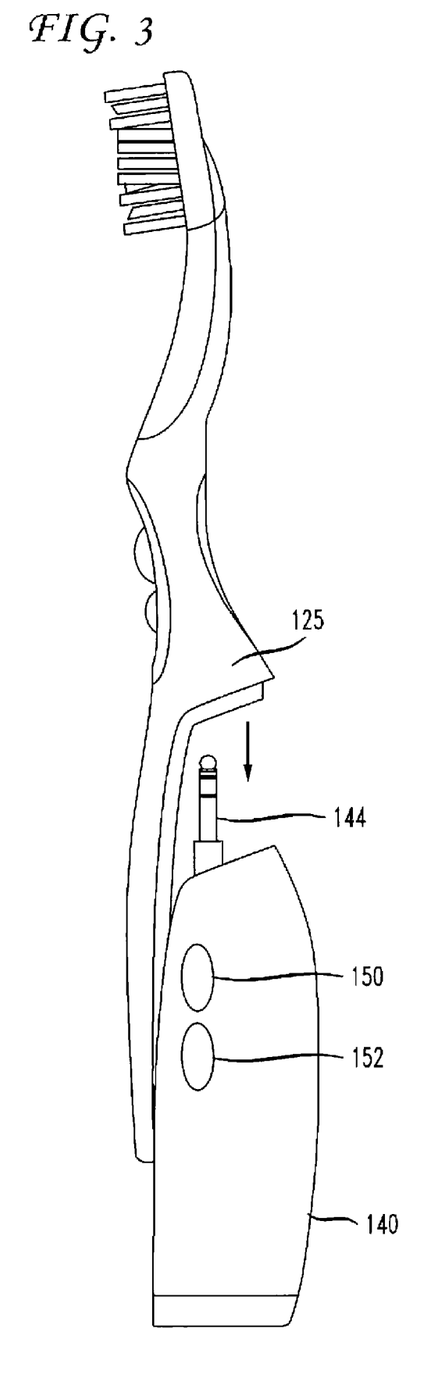
FIG. 3 is an exploded view of the toothbrush of FIG. 1 in accordance with at least one aspect of the present invention.

Referring to FIGS. 1-4, the removable storage unit 140 further comprises an input 144 for connection to an audio device 160, a digital memory device 146 (shown in dotted lines) for storing audio signals in digital form in which signal are received via the input 144. The input can take on a variety of forms. For example, in one arrangement, input 144 may be a standard headphone jack (i.e. 2.5 mm). Referring to FIG. 2, the removable storage unit 140 includes an output 148 in the form of a speaker positioned on the underside 149 of the unit 140 for audibly transmitting the digitally stored audio signals to the user's surroundings. The speaker can be of sealed construction for water resistance, for example. In additionally, the output 148 can be located at other parts of the storage unit 140. The storage unit 140 further includes a record button 150 for recording audio signals to the memory 146, and a play button 152 for playing the recorded audio signals. In operation, the play feature may incorporate a timed playback aspect as described herein. An electrical power source 154 (shown in dotted lines), such as a battery or the like, is provided in the storage unit 140 to power the record and playback features as well as any powered element in the toothbrush 120. For example, a vibration generator 122 (shown in dotted lines) may be located in the neck 123 to generate vibrations in the head 124. The generator 122 can be powered by the power source 154.

Alternatively, the storage unit 140 may plug into an outlet using a supplied cable connection (not shown). In accordance with at least one aspect of the present invention, the storage unit 140 of toothbrush 120 may be configured so that the functions associated with the record button 150 and the play button 152 may be operational as a single button. In such a configuration, storage unit 140 may determine whether the input 144 is connected to a signal source 160, in order to receive audio signal(s) when the single button is activated, or whether the input 144 is connected to toothbrush 120, in order to play the audio signal(s) when the single button is activated. Although shown as a push button type input, it should be understood by those skilled in the art that power buttons 128, 129, record button 150, and/or play button 152 may be any of a number of other types of input mechanisms or devices.

Figure 4:
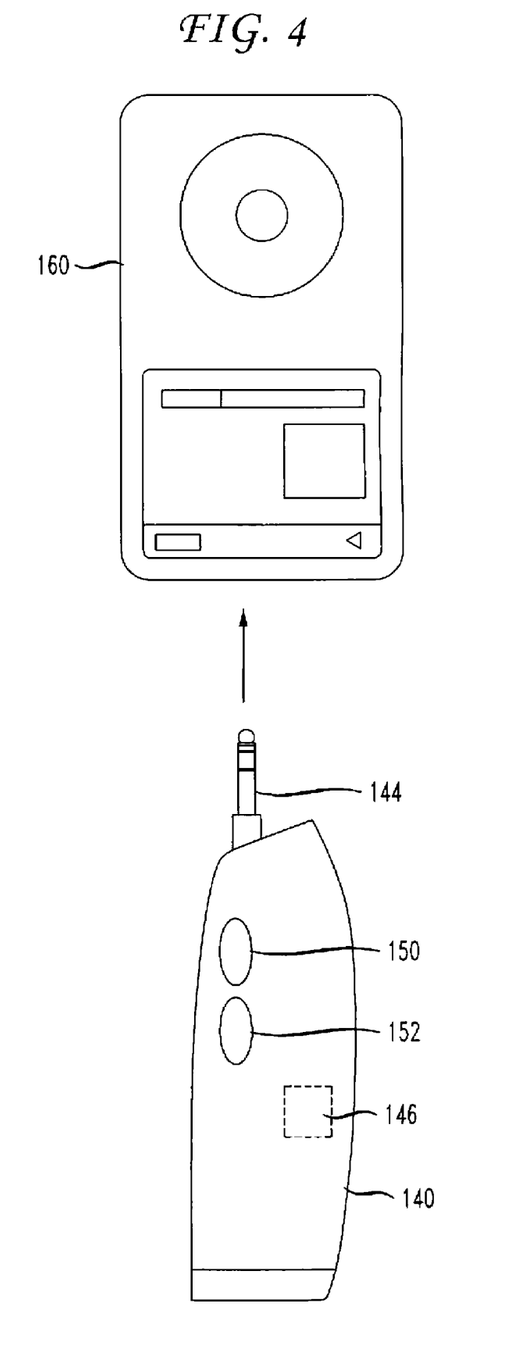
FIG. 4 is an exploded view of a connection arrangement of a storage unit of the toothbrush of FIG. 1 and a signal source in accordance with at least one aspect of the present invention.

In accordance with at least one aspect of the present invention, a user may connect toothbrush 120 to a signal source 160 (here shown as an APPLE® IPOD® for example) and activate the signal transfer from the source 160 to the memory 146 using a play button on the signal source (not shown) and the record button 150. The record button 150 may be depressed once to record a certain period of music, such as three minutes for example, or it may be held down for a period of time equal to the amount of music transferred.

The user then activates a timed playback of the stored music through the speaker 148 by pressing play button 152 to play music for, for example, two minutes upon pressing and holding button 152 for two seconds, or three minutes upon pressing and holding button 152 for three seconds. Other durations may be set, which can correlate with a time period other than two or three minutes, or it can designate a specific number of songs. Alternatively, toothbrush 120 may be configured so that a user may simply press the play button 152 if a timed playback is not desired. Nevertheless, while any type of musical or non-musical audio signals may be stored in the memory, the toothbrush 120 advantageously enables the user to play audio signals pleasurable to him or her. In this way, the user can have an enjoyable brushing experience and will likely brush his or her teeth for the entire playback duration.

In various scenarios of use, for children and teens, the audio signals may comprise audio digital webcasts, musical segments from a radio, satellite audio device, computer network (e.g., Internet), or the user's audio collection and the like. In one scenario, for adults, the audio signals may comprise information-based news summaries or stock reports for example that are automatically downloaded from the Internet. These various functions of the toothbrush enhance the brushing experience and enables longer duration brushing for improved oral hygiene. Any type of signal, such as audio and/or video, can be stored in the digital memory 146 of the toothbrush assembly 100, as long as the toothbrush assembly 100 includes an appropriate output to present such signal to a user. In one aspect, toothbrush assembly 100 may also include a display screen (not shown) to display video signals stored in the storage unit 140. Such uses, provides for musical videos to be played on the toothbrush 100, for example.

As should be understood by those skilled in the art, any number of types of external audio and/or video sources may be utilized including an MP3 player, a CD player, a cassette player, a computer, a satellite audio/video receiver, or handheld digital satellite audio device and/or other signal sources.

In the aspects of the oral device described to follow, the operation of recording and/or storing audio signals, such as music, in a storage unit, for future playback is in accordance with the embodiments of FIGS. 1-4. Furthermore, the described signal source may be any external source as long as the signals are capable of being communicated and transferred from the source to the toothbrush assembly. Thus, the connection between the storage unit and the signal source does not have to be a direct physical connection, but could be a wireless connection that utilizes, for example, Bluetooth® technology or the like. The various illustrative arrangements of toothbrushes described herein each creates an environment that makes tooth brushing enjoyable and more likely to be maintained for at least the dentist-recommended period of time.

In one operation, the storage unit 140 is removed from the body 125 (FIG. 3) and connected to a signal source 160 by a direct connection with the input 144. In the embodiments of FIG. 14 the input 144 generally comprises a headphone jack that extends outwardly from the storage unit 140. The input 144 is concealed within the body 125 of the toothbrush 120 when the storage unit 140 is connected thereto. Nevertheless, other input connections are contemplated, such as a Universal Serial Bus (USB) connector/adapter, which may be covered during use of the toothbrush 100 by a protecting cap (not shown), and which may function to both communicate with a signal source 160 and a power source 154 such as a recharging base (not shown). In this regard, the physical attachment of the input 144 with the body 125 does not result in signals being transferred from the storage unit 140 to the body 125. The outward extension of the input 144 allows the storage unit 140 to be directly connected or attached to the source 160 at a convenient location. The record button 150 and play button 152 function in a similar manner as described before, and a timed playback feature could be incorporated as described above.

The first power button 128 may be configured to power only the powered element (element 127, for example) of the brush 120, while the second power button 129 may be configured to simultaneously power the powered element 127 and generate a signal output through the speaker 148 for example. If there are no audio signals or the like stored in the memory 146, a user would only use the first power button 128. If it is desired to hear stored music or other audio while brushing, the second power button 129 would be used. Other power control schemes are contemplated as desired.

Figure 5:
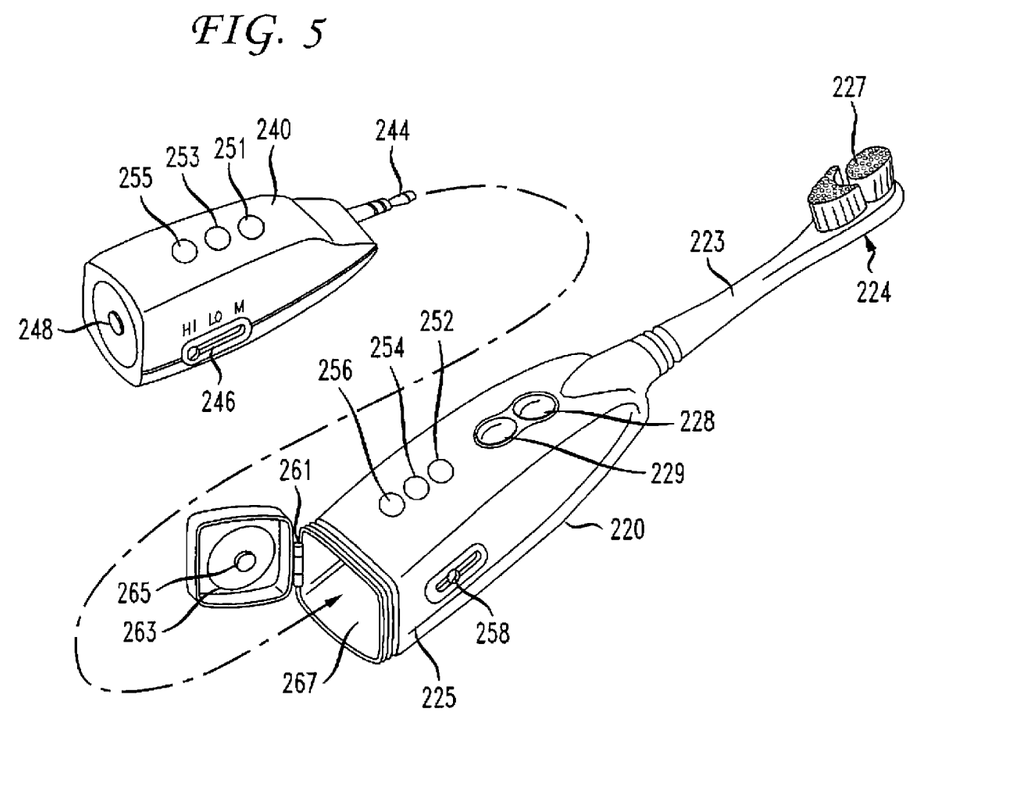
FIG. 5 is an exploded view of an example of a toothbrush in accordance with at least one aspect of the present invention.
Figure 6:
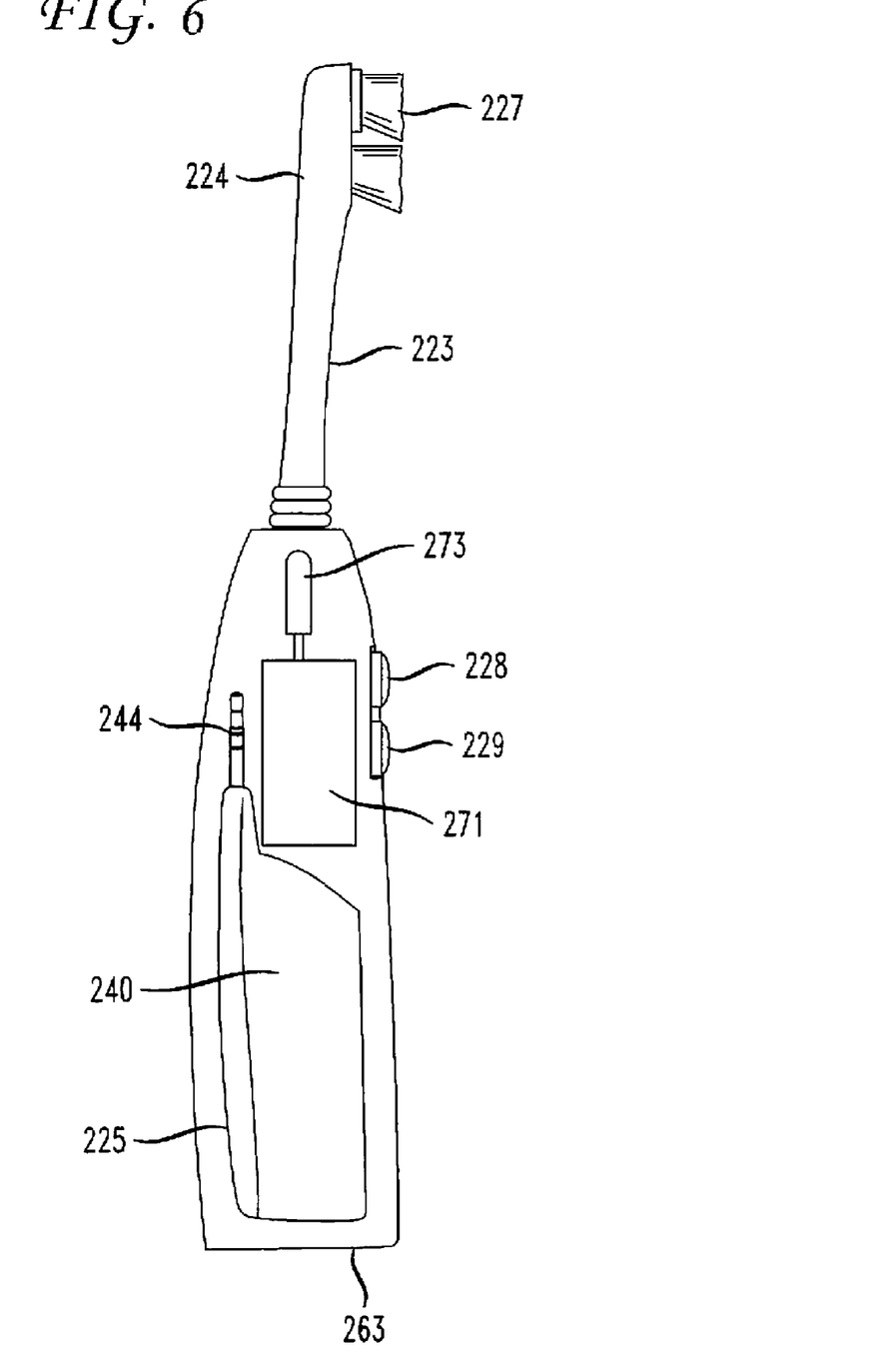
FIG. 6 is a cutaway side view illustrating internal components of the toothbrush of FIG. 5 in accordance with at least one aspect of the present invention.

FIGS. 5-6 illustrate another toothbrush assembly in accordance with at least one aspect of the present invention. The toothbrush assembly includes a power toothbrush 220 having a body 225, a removable storage unit 240 that may be inserted into an opening or cavity 267 of body 225, a first power button 228, and a second power button 229. The toothbrush 220 further includes a head 224 having cleaning elements 227. The cleaning elements 227 further comprise any known cleaning elements used in toothbrushes or other oral care implements, such as, but not limited to nylon bristles, tufts of bristles, bristle walls, elastomeric elements, and the like. The toothbrush 220 may be a power toothbrush including a motor/power source 271 (e.g., motor and battery combination, for example) that drives a shaft or rotor 273 for a powered element, such as movable cleaning elements 227 with a single activation/deactivation or "on/off" button 128. In an alternative configuration, toothbrush 220 may be a power toothbrush including motor/power source 271 that drives a powered element, such as movable cleaning elements 227 with an activation or "on" button 228 and a deactivation or "off" button 229. Toothbrush 220 is also shown to include a latching door 263 that is operatively connected to the body 225 by a latching mechanism 261. Door 263 is shown to include a grill 265 to allow for output of audio from a speaker. As should be understood by those skilled in the art, any of a number of different types and/or configurations of door 267 and/or latching mechanism 261 may be utilized. For example, door 263 may be threaded type so as to matingly engage the bottom of body 225 for closing the cavity 267. Nevertheless, other configurations are possible.

The removable storage unit 240 is similar in many respects to the removable storage unit 120. Storage unit 240 is configured to be housed within cavity 267 of the body 225 of toothbrush 220. In an alternative configuration described above, removable storage unit 140 is configured to be a portion of the outside surface of handle 126 or a portion of handle 126.

The removable storage unit 240 further comprises an input 244 for connection to a source device (not shown), a memory (not shown) for storing audio and/or video signal(s) received via the input 244, and an output 248 in the form of an integrated speaker positioned on the underside of the unit 240 for transmitting the stored signal(s) through grill 265 to the user's surroundings when the storage unit 240 is positioned within the body 225 of toothbrush 220. Input 244 may be a standard headphone jack. Storage unit 240 may further include a volume control 246 to allow a user to set the level of output through the speaker 248. The volume control 246 can be slide switch, dial and the like. When housed within the opening 263 of the body 225 of toothbrush 220, body 225, control 246 may be configured to be depressible or slidable through aperture control 258. The aperture control 258 may have thin elastomeric material covering so while maintaining a liquid seal of the cavity 267. In one exemplary arrangement, storage unit 240 includes a record button for recording the audio and/or video signal(s) to the memory. In the arrangement, the storage unit 240 may be configured to automatically record when sound from the source device (not shown) is detected. The sound from a source device triggers the storage unit 240 to record audio signals.

Storage unit 240 may include one or more a play buttons 251, 253, and 255 for playing recorded audio and/or video signal(s). For example, the storage unit 240 may store three separate songs. When housed within the opening 263 of the body 225 of toothbrush 220, button 251, 253, and 255 may be configured to be depressible through aperture 252, 254, and 256, respectively. The aperture 252, 254, 256 may have thin elastomeric material covering so that buttons 251, 253, and 255 may be depressible through body 225, while maintaining a liquid seal of the cavity 267.

Upon activation/interaction with button 251, a first audio file may be outputted to the speaker 248. Alternatively, if button 255 is depressed, a third audio file may be outputted to the speaker 248. The use of different audio files may allow different people to use the same storage unit 240 in different personal toothbrushes 240 and/or may allow a single user to store multiple songs for playback purposes. In one such example, a parent may want a child to hear an upbeat song when brushing in the morning to motivate the child to start her day, while the parent may want the child to hear a bedtime song when brushing before bedtime to motivate the child to get ready to sleep.

The play feature may incorporate a timed playback feature as described above. A power source (e.g., battery) may be provided in the storage unit 240 to power the record and playback features as well as any powered element in the toothbrush 220. For example, a vibration generator may be located in the neck of toothbrush 220 to generate vibrations in the head 224, which generator is powered by the power source.

Alternatively, storage unit 240 may plug into an outlet using a supplied cable connection (not shown). Although shown as a push button type input, it should be understood by those skilled in the art that power buttons 228, 229, play buttons 251, 253, and 255 may be any of a number of other types of input mechanisms.

Figure 7:
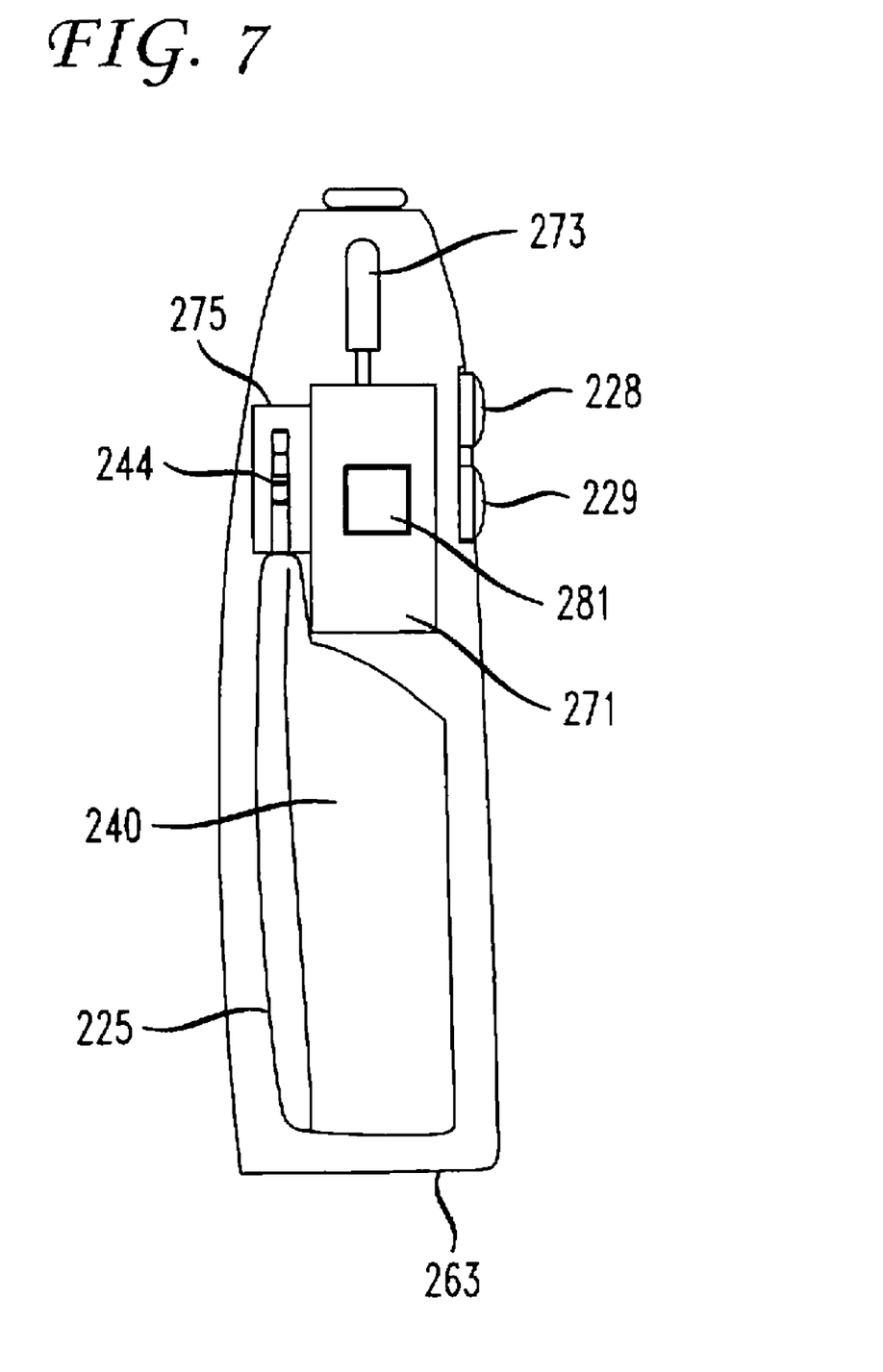
FIG. 7 is an enlarged internal view of a toothbrush in accordance with at least one aspect of the present invention.

As shown in FIG. 7, body 225 of toothbrush 220 may include an input socket 275. Input socket 275 may be configured to connect the power source 271 to the input 244. Input socket 275 may be a standard headphone plug input receiver. Input socket 275 may be configured internal to or external from the motor/power source 271. In the example shown in FIG. 7, input socket 275 is physically connected to motor/power source 271. In one arrangement, motor/power source 271 is attached to a connection determination unit 281. Connection determination unit 281 is configured to determine whether an input 244 is connected to the input socket 275. If an input 244 is detected by connection determination unit 281, toothbrush 220 is then configured to be able to play back audio and/or video signal(s) from storage unit 240 upon depression of a power button, such as power button 229.

Figure 8:
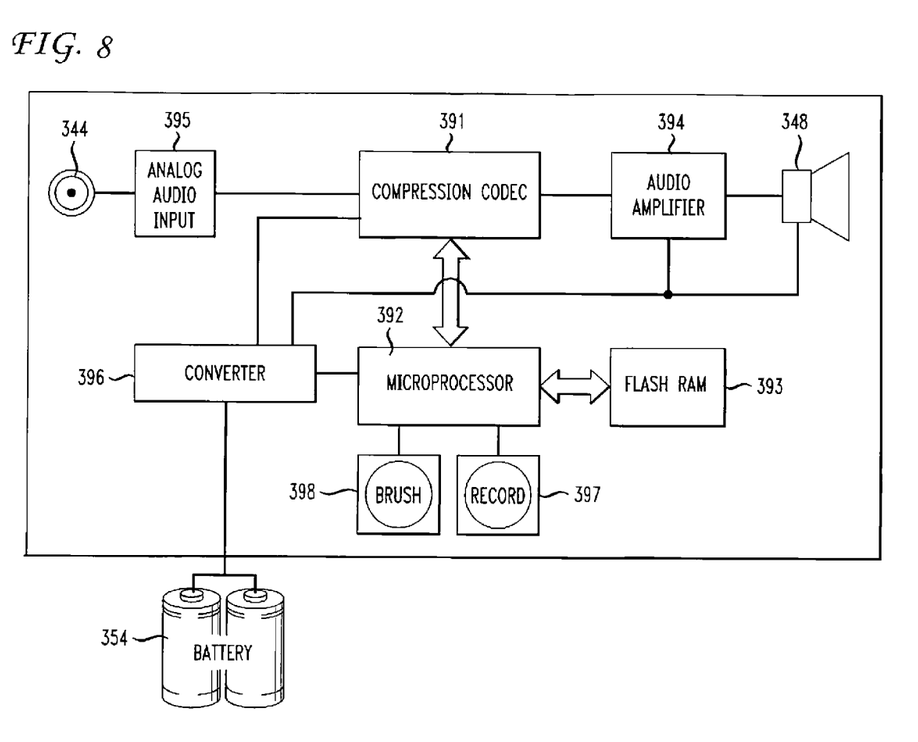
FIG. 8 is an example functional block diagram of components of a storage unit in accordance with at least one aspect of the present invention.

FIG. 8 illustrates an exemplary block diagram of components of a storage unit in accordance with at least one aspect of the present invention. One or more of the components of FIG. 8 may be included within one or more printed circuit boards. An illustrative printed circuit board may be 18 mm×50 mm with a 16 kHz sample rate. As shown, the components of a storage unit may include an input plug 344 in the form of a ⅛ inch stereo plug coupled to an analog audio input component 395. An integrated speaker 348, such as an 8 Ohm NXT speaker, may be coupled to an amplifier 294, such as a 2 Watt audio amplifier. Input received from the input plug 344 through the analog audio input component 395 is sent to a compression CODEC 391. Signal(s) for output are sent to the speaker 348 thought the amplifier 394 from the compression CODEC 391. Compression CODEC 391 is shown in communication with a microprocessor 392.

Microprocessor 392 is configured to perform all of the functions for processing signal(s), performing computer-readable instructions, and reading from and writing to a memory 393. As shown, microprocessor 392 communicates with a memory 393, such as a 2 MB flash RAM. Audio signals received via input plug 344 are stored in memory 393 and may be outputted to speaker 348. Power is provided by one or more batteries 354 to supply electrical power through a DC to DC converter 396 to one ore more components of the storage unit.

Recordation component 397 is shown coupled to microprocessor 392. Recordation component 397 may include instructions for the microprocessor 392 to record the audio signal(s) to memory 393 through input plug 344. Brush component 398 is shown coupled to microprocessor 392. Brush component 398 may include instructions for the microprocessor 392 to operate a motor (not shown) for a powered element (not shown) such as movable cleaning elements. As should be understood, instructions with respect to recordation component 397 and/or brush component 398 may be included within memory 393 and/or some other memory, such as a ROM memory.

In one aspect, an oral care device, such as a toothbrush, a tongue cleaner, and/or a flossing device, may be configured to automatically record sound when the sound from a source device is detected. The sound from a source device triggers the oral care to record the audio signal, i.e., the sound.

In one aspect, an oral care device may include an oral care region attached to a body with a portion of the body being configured for gripping by a user as described herein. This oral care device may further include a memory within the body of the device. The memory may be configured to store one or more audio signals.

A processor, which may be located within the body of the oral care device, may be configured to automatically record to the memory an audio signal from an external audio source, such as an MP3 player, a CD player, a radio, a television, and a person's voice. The processor may be configured to automatically record when the audio signal is detected. As such, the detection of the audio signal triggers the recording of the signal without any user selection to actually record the audio signal. Finally, a speaker may be included in the oral care device to output the stored audio signal. Any of a number of components described herein may be included in such an oral care device as well. Such components include, but are not limited to a play button on the body configured to activate the processor to send the stored audio signal to the speaker, the oral care region including tooth cleaning elements, a power source within the body, the oral care region including at least one powered element, and various operational buttons to activating/deactivating powered elements and/or the output of stored audio signals.

Figure 9:
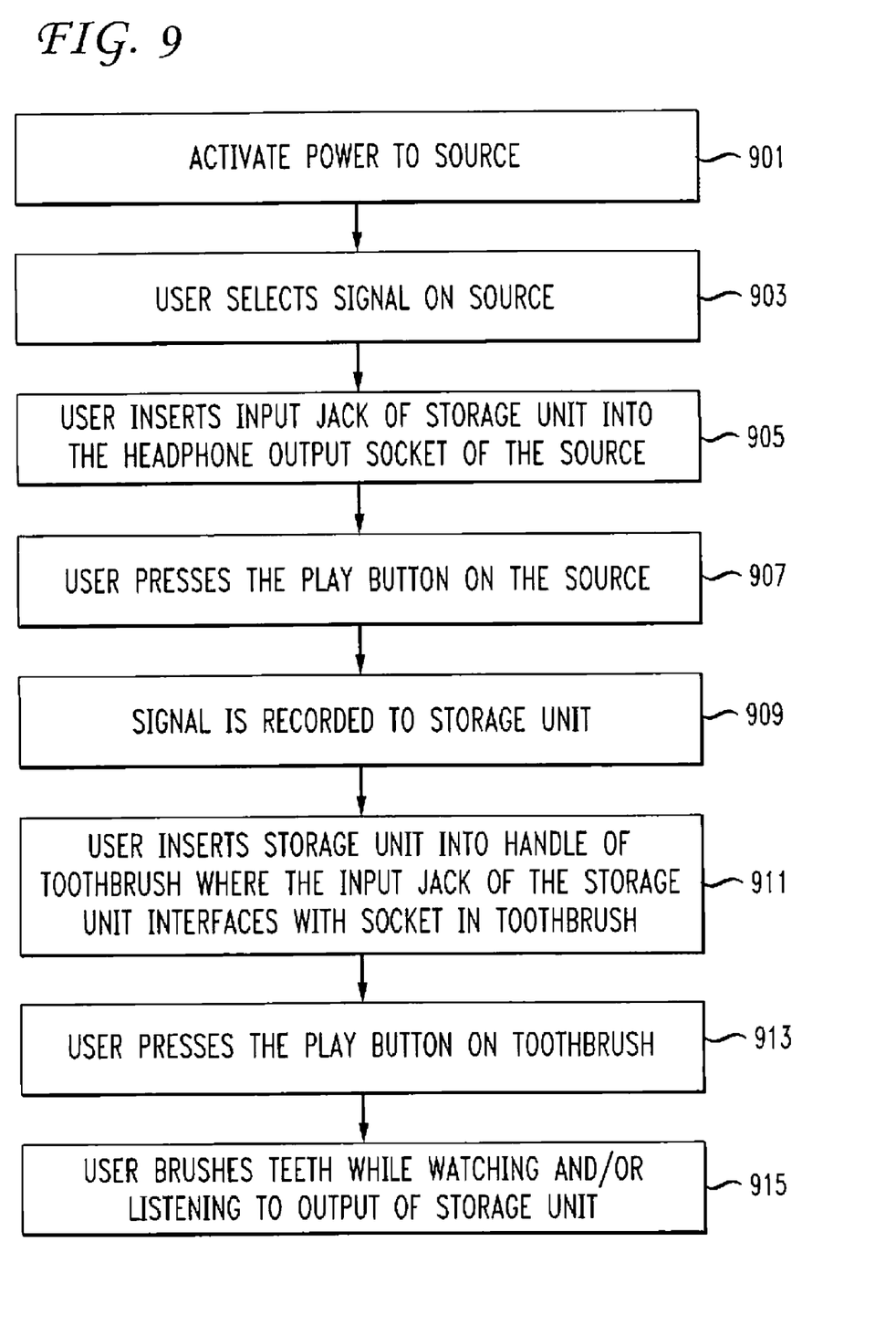
FIG. 9 is a flow chart of an illustrative method for transferring music or audio from a signal source to a toothbrush in accordance with at least one aspect of the present invention.

FIG. 9 is a flow chart of an illustrative method for transferring music from a signal source to a toothbrush assembly in accordance with at least one aspect of the present invention. The process starts at step 901 where power to an external source, such as a music player, is activated by a user. Such may be the case when a user turns on the music player. At step 903, the user selects a particular signal on the source of interest. In one example, this may be a case where the user selects a particular 2-4 minutes song to be recorded. Proceeding to step 905, the user inserts the input headphone jack of a storage unit, such as input 244 of storage unit 240, into the headphone output socket of the source device, such as source device 160. At this point, although not shown, the user may set the output level of the source device to medium or low.

At step 907, the user presses the play button on the source device to play the selected song of interest. The storage unit may be configured to trigger recordation of the song when sound is detected. Alternatively, a record button, such as record button 150, associated with the storage unit may be depressed by the user to start the recordation process. In any configuration, at step 909, the selected signal of interest is recorded in the memory of the storage unit, such as memory 393. While the storage unit is recording, a previous file or song can be automatically overwritten. Upon completion of the recordation of the song and proceeding to step 911, the user inserts the storage unit into the handle of a toothbrush where the input jack of the storage unit interfaces with a socket in the toothbrush. Such an illustrative configuration is shown in FIG. 7 where input socket 275 of toothbrush 220 interfaces with input 244 of storage unit 244. In this example, storage unit 244 is shown in the body 225 of toothbrush 220.

At step 913, the user presses the play button on the toothbrush. In one such example shown in FIG. 6, the user may depress power button 229 to activate the output of music. Finally, at step 915, the user brushes her teeth with the toothbrush while watching and/or listening to output from the storage unit. For example, if a song of interest has been recorded, the song is outputted through a speaker, such as speaker 248. In one configuration, the time for the song may correlate to the desired amount of time for the user to brush her teeth, such as two minutes.

Referring to FIGS. 1 and 5, in another aspect, a vibratory device 122 can be provided to vibrate the toothbrush 120, 220 or a portion thereof, such as the head 124, 224 or a portion thereof. The vibration-producing device can be used to vibrate tooth cleaning elements 127, 227 and/or soft tissue cleaning elements.

A wide variety of vibratory devices can be used to produce vibrations over a wide range of frequencies to meet the needs of a particular application. Various types of vibratory devices are commercially available, such as transducers. One example of a vibratory device provides frequencies in the range of about 100 to 350 kHz. The vibration frequencies may be of different waveforms, including sinusoid, square, sawtooth and the like. Nevertheless, other values and waveforms are possible. A vibratory device may be located in head of the toothbrush or neck thereof. When activated, vibratory device is powered by battery (and controlled by electronics on circuit board or switching system) so as to induce vibrations in head of the toothbrush and thereby enhances teeth-cleaning action imparted by the tooth cleaning elements. In alternate embodiments, a vibratory device may include a micro motor attached to a shaft, with the shaft coupled to an eccentric rotating about an axis parallel to the longitudinal axis of the toothbrush. In still other embodiments, a vibratory-producing device includes an eccentric that is driven by a micro motor in a translatory manner.

A switch, such as a button 128, 228, toggle switch, rotating dial, or the like, can be provided for activating the vibratory device. A vibratory device often has a power source, such as a battery. Activating the switch can cause the vibration-producing device to operate for a user-defined interval (e.g., during the time that a button is depressed or a switch is in an engaged position), or alternatively can activate a timing circuit that causes the vibratory device to operate for a predetermined interval. If a timing circuit is used, the associated interval either may be preset or may be adjustable, e.g., by a user-activated rotating dial.

In one embodiment, referring to FIGS. 1, 3, 5 and 6, a ratio of the length of the neck 123, 223 and head 124, 224 to the height of the toothbrush (measured from the distal bottom end 149 to the distal top of head 124, 224) ranges from 1:10 to 2:5. In another example, the noted neck/head length to the toothbrush height ratio ranges from 1:20 to 1:30. Nevertheless, other values of the noted ratios are possible. In one embodiment, the external height of the toothbrush ergonomically sized for children ranges from about 160 mm to 200 mm. In other arrangements, the height of the toothbrush ranges from about 160 mm to 194 mm; to less than 194 mm or 190 mm. Nevertheless, other heights of the toothbrush assembles are possible. In one arrangement, the width of the handle 10 can range between 19 mm to 28 mm. In another arrangement, the depth of the handle 10 ranges between 19 mm to 27 mm. In other embodiments, the depth ranges between 19 mm to 21 mm. In a cylindrical configuration, the handle 10 may have a diameter ranging from 19 mm to 28 mm. Nevertheless, other values are possible. These ergonomic configurations provides for a toothbrush to have a neck/head length to reach within the depth of the oral cavity, while balancing the need for musculoskeletal strength of a child to manipulate the toothbrush. Accordingly, these configurations or combination thereof enable an easily maneuverable electric toothbrush for children and provides for an enjoyable brushing experience to improve oral hygiene.

It is understood that designations such as "first" and "second" are for illustrative purposes and can be interchanged. While the invention has been described with respect to specific examples including presently preferred modes of carrying out the invention, those skilled in the art will appreciate that there are numerous variations and permutations of the above described systems and techniques. Thus, the spirit and scope of the invention should be construed broadly as set forth in the appended claims.

We claim:

1. A toothbrush comprising:
an oral care region attached to a body, a portion of the body being configured for gripping by a user;
a storage unit housing including an input for receiving one or more signals from an external signal source, a memory for storing the one or more signals received via the input, an output for transmitting the stored one or more signals and a power source; and
wherein the storage unit housing is configured to be removably housed within a cavity of the body.

2. The toothbrush of claim 1, wherein the storage unit housing includes a coder/decoder for processing the one or more signals.

3. The toothbrush of claim 1, wherein the one or more signals are audio signals; and the storage unit housing further comprises a processor for recording the audio signals to the memory.

4. The toothbrush of claim 3, further comprising a record button on the storage unit housing for activating the processor.

5. The toothbrush of claim 1, wherein the oral care region comprises tooth cleaning elements.

6. The toothbrush of claim 1, wherein the output is a speaker disposed at an end of the storage unit housing opposing the input.

7. The toothbrush of claim 6, wherein the storage unit housing further includes a volume control for setting a level of output through the speaker.

8. The toothbrush of claim 1, wherein the storage unit housing is configured to be removably received in more than one body.

9. The toothbrush of claim 1, wherein the oral care region comprises at least one powered element operably connected to the power source in the storage unit housing.

10. The toothbrush of claim 1, wherein the body further comprises a power source for powering at least one powered tooth cleaning element in the oral care region, the power source of the body being different from the power source of the storage unit housing.

11. The toothbrush of claim 1, wherein the oral care region comprises at least one tooth cleaning element, wherein the portion of the body and a portion of the storage unit housing forms a handle.

12. The toothbrush of claim 11, wherein the output is a speaker disposed on a bottom portion of the handle.

13. The toothbrush of claim 1, wherein the input extends outwardly from the detachable storage unit housing.

14. The toothbrush of claim 13, further comprising a mechanical connection between the input and the body.

15. The toothbrush of claim 14, wherein the input is received within a socket in the body.

16. The toothbrush of claim 1, wherein the storage unit housing samples an audio signal to digitize for subsequent audio presentation.

17. The toothbrush of claim 1, wherein the one or more signals are outputted from the memory in response to interaction of a button on the body.

18. The toothbrush of claim 1, wherein the body includes a latching door to permit insertion of the detachable storage unit housing therein.

19. The toothbrush of claim 1, wherein the storage unit housing further includes a microprocessor configured to automatically record the one or more signals from the external signal source upon a determination of sound outputted from the external signal source.

20. The toothbrush of claim 1, wherein the body includes a vibratory device.

21. The toothbrush of claim 1, wherein the storage unit housing further comprises one or more user selectable buttons for transmitting the one or more stored signals to the output; and wherein the body has one or more apertures aligned with the one or more buttons on the storage unit housing when the storage unit housing is housed in the cavity of the body, the one or more buttons being depressible through the one or more apertures.

22. The toothbrush of claim 21, wherein the one or more apertures are covered with a thin elastomeric material to maintain a liquid seal of the cavity of the body.

* * * * *